United States Patent

Hirai et al.

[11] Patent Number: 5,886,211
[45] Date of Patent: Mar. 23, 1999

[54] PROCESS FOR PRODUCING 2-(HALOMETHYL)PHENYLACETIC ACID ESTERS

[75] Inventors: Kenji Hirai, Kanagawa; Katsuyuki Masuda, Ibaraki; Yoshihiro Takao, Shizuoka; Masahide Sugiyama, Shizuoka; Yukio Ono, Shizuoka; Masahumi Matsuzawa, Chiba, all of Japan

[73] Assignees: Sagami Chemical Research Center, Kanagawa; Iharanikkei Chemical Industry Co., Ltd, Shizuoka, both of Japan

[21] Appl. No.: 981,449

[22] PCT Filed: Jun. 19, 1996

[86] PCT No.: PCT/JP96/01677

§ 371 Date: Mar. 18, 1998

§ 102(e) Date: Mar. 18, 1998

[87] PCT Pub. No.: WO97/00850

PCT Pub. Date: Jan. 9, 1997

[30]   Foreign Application Priority Data

Jun. 20, 1995  [JP]  Japan .................... 7-176831
Apr. 10, 1996  [JP]  Japan .................... 8-087742
Apr. 10, 1996  [JP]  Japan .................... 8-087743
Apr. 10, 1996  [JP]  Japan .................... 8-113190
Jun. 10, 1996  [JP]  Japan .................... 8-147110

[51] Int. Cl.$^6$ ............................................ C07C 69/76
[52] U.S. Cl. ................................ 560/105; 549/290
[58] Field of Search ........................ 549/290; 560/105

[56]   References Cited

FOREIGN PATENT DOCUMENTS 54-138536  10/1979  Japan ................... C07C 101/04
59-163370   9/1984  Japan ................... C07D 217/24

OTHER PUBLICATIONS

Chem Abstracts online printout; 1981:103198, Pandey et al.
Journal of the American Chemical Society, vol. 102, No. 12, (1980), A. Cowell and J.K. Stille "Synthesis of Lactones by the Palladium–Catalyzed Carbonylation of Halo Alcohols", pp. 4193–4198.

*Primary Examiner*—Samuel Barts
*Attorney, Agent, or Firm*—Sughrue, Mion, Zinn, Macpeak & Seas, PLLC

[57]   ABSTRACT

2-(Halomethyl)phenylacetic acid esters (3) which are useful as intermediates for producing agricultural fungicides are produced efficiently and conveniently by reacting a 3-isochromanone derivative (1) with a hydrogen halide and an alcohol or reacting (1) with a halomethyl alkyl ether and then reacting the product with an alcohol in the presence of a base. The starting compound, 3-isochromanone (1), is produced in good yield by reacting an α,α'-o-xylene dihalide (4) with carbon monoxide and water in an organic solvent in the presence of a palladium catalyst and an inorganic base and then treating the product with an acid.

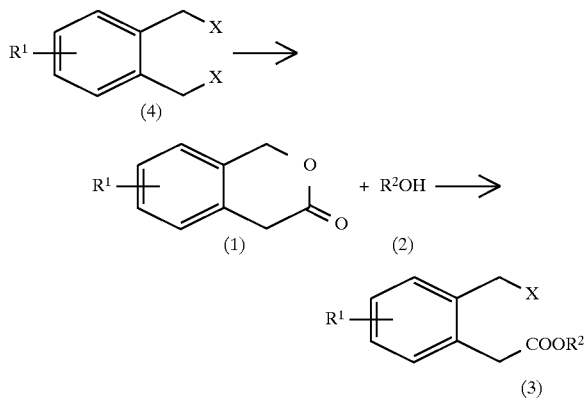

12 Claims, No Drawings

PROCESS FOR PRODUCING 2-(HALOMETHYL)PHENYLACETIC ACID ESTERS

This application is a 371 of PCT/JP96/01677 filed Jun. 19, 1996.

1. Field of the Invention

This invention relates to a process for producing 2-(halomethyl)phenylacetic acid esters which are intermediates for synthesizing cephalosporin antibiotics and are also expected to be intermediates for synthesizing fungicides for agricultural use, and relates to a process for producing 3-isochromanones which are starting materials for producing the 2-(halomethyl)phenylacetic acid esters.

2. Background of the Art

Among the known processes for synthesizing 2-(halomethyl)phenylacetic acid esters is a process starting with xylene (Japan Kokai Tokkyo Koho, JP 59-193370), but it is not deemed useful because of involvement of many steps and poor selectivity.

A process comprising reacting 3-isochromanone with α,α,α'-trichlorodimethyl ether into 2-(chloromethyl)phenylacyl chloride is also known (*J. Prakt. Chem.*, 12 (1966)). However, the yield is low, and a further reaction with an alcohol is required for producing 2-(chloromethyl)phenylacetic acid esters. There is no report on synthesis of 2-(halomethyl)pehnylacetic acid esters using 3-isochromanone as a starting material.

Known processes for producing 3-isochromanones referred to above as a starting material include (1) chloromethylation of a substituted phenylacetic acid (*J. Chem. Soc.*, 178 (1927)), (2) reaction between o-bromomethylbenzyl alcohol and carbon monoxide in the presence of a palladium catalyst (*J. Amer. Chem. Soc.*, 4193 (1980)), (3) oxidation of 2-indanone with a peroxide, such as metachloroperbenzoic acid, in a solvent in accordance with Bayer-Villiger rearrangement (*Synthesis*, 818 (1981)), (4) cyclization of α-methoxy-α'-cyano-o-xylene with sulfuric acid (*J. Chem. Soc.*, 2819 (1954)), (5) cyclization of ethyl o-ethoxycarbonylphenylacetate with diisobutylaluminum hydride followed by oxidation (*Tetrahydron Letters*, 2359 (1973)), and (6) reaction between o-methylbenzyl alcohol and butyl lithium followed by reaction with carbon dioxide (*Tetrahydron Letters*, 1233 (1983)).

The process (1) has a poor yield and is not necessarily regarded advantageous for industrial production. The processes (2) to (6) involve difficulties in preparing the starting materials used so that the synthesis of 3-isochromanones must begin with purification of the starting material. These processes therefore comprise an increased number of steps, which is disadvantageous for cost and yield, and none of them can be a useful process for industrially producing 3-isochromanones.

DISCLOSURE OF THE INVENTION

The inventors have conducted various studies for providing industrial and economical processes for producing 2-(halomethyl)phenylacetic acid esters and 3-isochromanones that are starting materials of the 2-(halomethyl)phenylacetic acid esters. As a result, it has now been found that 2-(halomethyl)phenylacetic acid esters can be prepared selectively and in good yield under mild conditions by (1) reacting a 3-isochromanone with a hydrogen halide and an alcohol or (2) reacting a 3-isochromanone with a dihalomethyl alkyl ether and reacting the reactant with an alcohol. It has also been found that the starting 3-isochromanones can be prepared in a short time with good selectivity and yield by reacting an o-xylene dihalide derivative, which is an industrially economical material, with carbon monoxide and water in an organic solvent in the presence of a hydrogen halide capturing agent and a catalyst.

That is, the present invention relates to a process for producing 2-(halomethyl)phenylacetic acid esters represented by the following formula (3):

(3)

wherein $R^1$ represents a hydrogen atom, a halogen atom, an alkyl group having 1 to 6 carbon atoms, or an alkyloxy group having 1 to 6 carbon atoms; $R^2$ represents an alkyl group having 1 to 6 carbon atoms; and X represents a halogen atom, which comprises reacting a 3-isochromanone represented by the following formula (1):

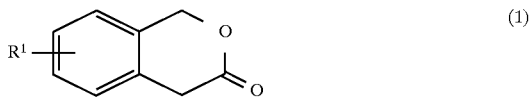
(1)

wherein $R^1$ has the same meaning as defined above, with a hydrogen halide and an alcohol represented by the following formula (2):

$$R^2OH \quad (2)$$

wherein $R^2$ is the same meaning as defined above.

Furthermore, the present invention relates to a process for producing 2-(halomethyl)phenylacetic acid esters represented by the following formula (3):

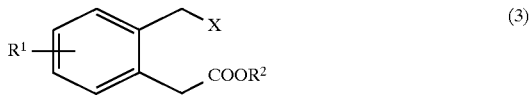
(3)

wherein $R^1$ represents a hydrogen atom, a halogen atom, an alkyl group having 1 to 6 carbon atoms, or an alkyloxy group having 1 to 6 carbon atoms; $R^2$ represents an alkyl group having 1 to 6 carbon atoms; and X represents a halogen atom, which comprises:
  reacting a 3-isochromanone represented by the following formula (1):

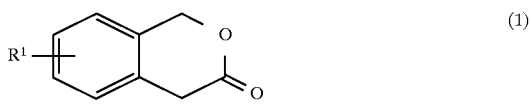
(1)

wherein $R^1$ is the same meaning as defined above,
with a dihalomethyl alkyl ether to obtain a reactant; and then
reacting the reactant with an alcohol represented by the following formula (2):

$$R^2OH \quad (2)$$

wherein $R^2$ is the same meaning as defined above,
in the presence of a base.

Moreover, the present invention relates to a process for producing 3-isochromanones represented by the following formula (1):

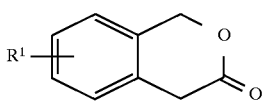

(1)

wherein $R_1$ represents a hydrogen atom, a halogen atom, an alkyl group having 1 to 6 carbon atoms, or an alkyloxy group having 1 to 6 carbon atoms, which comprises:
reacting an α,α'-o-xylene dihalide derivative represented by the following formula (4):

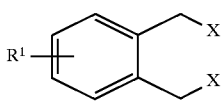

(4)

wherein $R^1$ is the same meaning as defined above; and X represents a halogen atom,
with carbon monoxide and water in the presence of a hydrogen halide capturing agent and a catalyst to obtain a reactant; and then
treating the reactant with an acid.

In the first process for producing 2-(halomethyl) phenylacetic acid esters using a hydrogen halide, it seems that the reaction between a 3-isochromanone and a hydrogen halide results in opening of the lactone ring to provide, as an intermediate, a 2-(halomethyl)phenylacetic acid represented by the following formula (5):

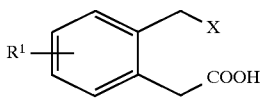

(5)

wherein $R^1$ and X are the same meanings as defined above. The 2-(halomethyl)phenylacetic acid then reacts with the alcohol represented by formula (2) to obtain the 2-(halomethyl)phenylacetic acid esters represented by formula (3). In the first process, while the alcohol may be added after the reaction between the 3-isochromanone and the hydrogen halide, it is preferable for the sake of operating convenience that the reaction with the hydrogen halide be in the presence of the alcohol.

In the second process for producing 2-(halomethyl) phenylacetic acid esters using a dihalomethyl alkyl ether, the reaction between the 3-isochromanone and the dihalomethyl alkyl ether would result in opening the lactone ring to provide, as an intermediate, a 2-(halomethyl)phenylacetyl halide represented by the following formula (6):

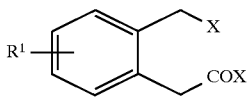

(6)

wherein $R^1$ and X are the same meanings as defined above.

Then, the intermediate reacts with the alcohol in the presence of a base to obtain the 2-(halomethyl)phenylacetic acid esters.

In either process, the intermediate product (i.e., the 2-(halomethyl)phenylacetic acid derivative or 2-(halomethyl)phenylacetyl halide derivative), though it could be isolated, can be allowed to react with the alcohol without being isolated thereby achieving conversion to the 2-(halomethyl)phenylacetic acid esters through one step.

In formulae (1), (3), (5), and (6), the halogen atom represented by $R^1$ includes a fluorine atom, a chlorine atom, and a bromine atom. The alkyl group represented by $R^1$ includes straight-chain or branched alkyl groups having 1 to 6 carbon atoms, such as a methyl group, an ethyl group, a propyl group, an isopropyl group, a butyl group, a sec-butyl group, an isobutyl group, a t-butyl group, a pentyl group, a neopenyl group, a hexyl group, and a 1-ethylbutyl group. The alkyloxy group represented by $R^1$ includes straight-chain or branched alkyloxy groups having 1 to 6 carbon atoms, such as a methoxy group, an ethoxy group, a propyloxy group, an isopropyloxy group, a butyloxy group, a sec-butyloxy group, an isobutyloxy group, a t-butyloxy group, a pentyloxy group, a neopentyloxy group, a hexyloxy group, and a 1-ethylbutyloxy group.

In formulae (2) and (3), the alkyl group represented by $R^2$ includes straight-chain or branched alkyl groups having 1 to 6 carbon atoms, such as a methyl group, an ethyl group, a propyl group, an isopropyl group, a butyl group, a sec-butyl group, an isobutyl group, a t-butyl group, a pentyl group, a neopenyl group, a hexyl group, and a 1-ethylbutyl group.

The hydrogen halide that is the reaction reagent used in the first process includes hydrogen fluoride, hydrogen chloride, hydrogen bromide, and hydrogen iodide. From the standpoint of reaction efficiency, hydrogen chloride or hydrogen bromide is preferred. To obtain the objective compound in good yield, the hydrogen halide is suitably used in an amount of 1 to 30 molar equivalents to the reaction substrate. The halogen atom represented by X in the product, 2-(halomethyl)phenylacetic acid ester derivative represented by formula (3), is the same as in the hydrogen halide used.

The dihalomethyl alkyl ether that is a reaction reagent used in the second process includes dichloromethyl methyl ether, dibromomethyl methyl ether, dichloromethyl ethyl ether, dibromomethyl ethyl ether, dichloromethyl propyl ether, dibromomethyl propyl ether, dichloromethyl isopropyl ether, dibromomethyl isopropyl ether, dichloromethyl butyl ether, dibromomethyl butyl ether, dichloromethyl isobutyl ether, dibromomethyl isobutyl ether, dichloromethyl t-butyl ether, dibromomethyl t-butyl ether, dichloromethyl pentyl ether, dibromomethyl pentyl ether, dichloromethyl hexyl ether, and dibromomethyl hexyl ether. Dichloromethyl methyl ether or dibromomethyl methyl ether is preferred for reaction efficiency. An equivalent of the dihalomethyl alkyl ether to the starting material would be enough stoichiometrically, but use of 1 mole or more per mole of the reaction substrate is preferred for obtaining the objective product in good yield.

The halogen atom represented by X in the product, 2-(halomethyl)phenylacetic acid esters represented by formula (3), is the same as in the dihalomethyl alkyl ether used.

The alcohol represented by formula (2) used in the first and second processes includes straight-chain or branched alcohols having 1 to 6 carbon atoms, such as methyl alcohol, ethyl alcohol, propyl alcohol, isopropyl alcohol, butyl alcohol, isobutyl alcohol, t-butyl alcohol, sec-butyl alcohol, pentyl alcohol, and hexyl alcohol.

The reaction temperature in the first process is selected from the range of from −20° to 80° C. To secure smooth progress of the reaction, a temperature of from 0° to 40° C. is preferred.

In the first process, the alcohol as a reaction reagent can serve as a solvent, or an appropriate solvent can be used. Suitable organic solvents include halogen-containing solvents, such as chloroform and dichloromethane; aliphatic hydrocarbons, such as pentane, hexane, octane, decane, dodecane, tridecane, and tetradecane; aromatic solvents, such as toluene, xylene, chlorobenzene, dichlorobenzene, and tetralin; and mixtures thereof. Any other solvents can be used as long as no adverse influence is exerted on the reaction.

The base which can be used in the second process includes inorganic salts, such as sodium carbonate and potassium carbonate; and tertiary amines, such as trimethylamine, triethylamine, tripropylamine, tributylamine, tripentylamine, trihexylamine, triheptylamine, trioctylamine, triphenylamine, and pyridine. Any other bases can be used in the reaction as far as no adverse influences is produced on the reaction.

The reaction temperature in the second process is selected from the range of from 0° to 100° C. To secure smooth progress of the reaction, a temperature of from room temperature to 60° C. is preferred.

The reaction of the second process can be carried out without a solvent, or an appropriate organic solvent can be used. Suitable organic solvents include halogen-containing solvents, such as chloroform and dichloromethane; aliphatic hydrocarbons, such as pentane, hexane, octane, decane, dodecane, tridecane, and tetradecane; aromatic solvents, such as toluene, xylene, chlorobenzene, dichlorobenzene, and tetralin; and mixtures thereof. Any other solvents can be used as long as no negative influence is exerted on the reaction.

The 2-(halomethyl)phenylacetic acid ester derivative (3) prepared by the processes of the present invention can be converted to fungicides for agricultural use by, for example, successively reacting with a substituted phenol, an alkyl nitrite, and dimethyl sulfate (see, e.g., EP 0493711-A).

The 3-isochromanones can be produced by reacting an α,α'-o-xylene dihalide derivative represented by the following formula (4):

(4)

wherein $R^1$ and X are the same meanings as defined above, with carbon monoxide and water in an organic solvent in the presence of a hydrogen halide capturing agent and a catalyst to obtain a reactant; and then treating the reactant with an acid.

The process for producing the 3-isochromanones seems to proceed as follows. One of the halomethyl groups of the α,α'-o-xylene dihalide derivative is oxidatively added to the catalyst to form a benzyl complex. After carbon monoxide insertion, the complex is hydrolyzed with a base to form a carboxylic acid salt. At the same time, the other halomethyl group is converted into a salt of a hydroxymethyl group by the action of the base thereby to provide, as an intermediate product, an o-hydroxymethylphenylacetic acid salt represented by the following formula (7):

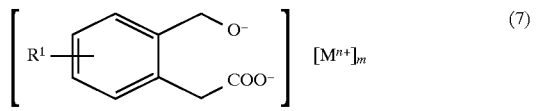

(7)

wherein $R^1$ is the same meaning as defined above; M represents an alkali metal or an alkaline earth metal; when n is 1, m is 2; when n is 2, m is 1. It is considered that the resulting o-hydroxymethylphenylacetic acid salt easily undergoes esterification within the molecule thereof under an acidic condition to obtain objective 3-isochromanones. Accordingly, the intermediate product, o-hydroxymethylphenylacetic acid salt, could be isolated but can be treated as such, without being isolated, with an acid to obtain objective 3-isochromanones.

The halogen atom represented by $R^1$ in formulae (1), (4) and (7) includes a fluorine atom, a chlorine atom, and a bromine atom. The alkyl group represented by $R^1$ includes straight-chain or branched alkyl groups having 1 to 6 carbon atoms, such as a methyl group, an ethyl group, a propyl group, an isopropyl group, a butyl group, a sec-butyl group, an isobutyl group, a t-butyl group, a pentyl group, a neopenyl group, a hexyl group, and a 1-ethylbutyl group. The alkyloxy group as represented by $R^1$ includes straight-chain or branched alkyloxy groups having 1 to 6 carbon atoms, such as a methoxy group, an ethoxy group, a propyloxy group, an isopropyloxy group, a butyloxy group, a sec-butyloxy group, an isobutyloxy group, a t-butyloxy group, a pentyloxy group, a neopentyloxy group, a hexyloxy group, and a 1-ethylbutyloxy group.

The catalyst to be used in the production of the 3-isochromanones includes palladium catalysts, cobalt catalysts, and iron catalysts. Examples of the palladium catalysts include palladium (II) or (0) complexes, such as palladium chloride, palladium bromide, palladium iodide, palladium cyanide, palladium acetate, palladium nitrate, dichlorobis(trimethylphosphine)palladium, dibromobis(trimethylphosphine)palladium, dichlorobis(triethylphosphine)palladium, dibromobis(triethylphosphine)palladium, diiodobis(triethylphosphine)palladium, dichlorobis(tripropylphosphine)palladium, dichlorobis(triisopropylphosphine)palladium, dibromobis(triisopropylphosphine)palladium, dichlorobis(tributylphosphine)palladium, dichlorobis(triphenylphosphine)palladium, dibromobis(triphenylphosphine)palladium, diacetatobis(triphenylphosphine)palladium, dichlorobis(tri-o-tolylphosphine) palladium, dichlorobis-(tri-o-methoxyphenylphosphine)palladium, dichlorobis(dimethylphenylphosphine) palladium, dichlorobis(diethylphenylphosphine)palladium, dibromobis(diethylphenylphosphine)palladium, dichlorobis(dibutylphenylphosphine)palladium, dichlorobis{tris(dimethylamino)-phosphine}palladium, dichlorobis(trimethyl phosphite)palladium, dichloro{1,2-bis(diphenylphosphino)ethane}-palladium, dihydrotetrachloropalladium, sodium tetrachloropalladate, potassium tetrachloropalladate, potassium tetrabromopalladate, bis[{3-sodium sulfonato)-phenyl}diphenylphosphine}dichloropalladium, ammonium tetrachloropalladate, ammonium hexachloropalladate, dichlorodiamminepalladium, dichlorobis(benzonitrile)palladium, dibromobis(benzonitrile)palladium, diiodobis(benzonitrile)palladium, dichlorobis(acetonitrile)palladium, palladium acetate, palladium trifluoroacetate, bis(triphenylphosphine)palladium diacetate, dichloro(cycloocta-1,5-diene)palladium, dicarbonyldichloropalladium, bisacetylacetonatopalladium, bis(t-butylisocyanide)dichloropalladium, di-μ-chloro-dichlorobis(triphenylphosphine)dipalladium, di-μ-chloro-dichlorobis(methylisocyanide)dipalladium, tetrakis(triphenylphosphine)palladium, bis(dibutylphenylphosphine)palladium, bis(tributylphosphine)palladium, bis(tricyclohexylphosphine)palladium, tetrakis(triphenyl phosphite)palladium, tetrakis(triethyl phosphite)palladium, carbonyltris(triphenylphosphine)palladium, bis{1,2-bis(diphenylphosphino)ethane}palladium, tris(dibenzylideneacetone)dipalladium, ($\eta^2$-ethylene)bis(triphenylphosphine)palladium, and bis(cycloocta-1,5-diene)palladium.

Examples of the cobalt catalysts include cobalt chloride, octacarbonyldicobalt, dodecacarbonyltetracobalt, hexacarbonylbis(triphenylphosphine)dicobalt, sodium tetracarbonylcobaltate, and potassium tetracarbonylcobaltate.

Examples of the iron catalysts include iron chloride, iron acetate, bis(cyclopentadiphenyl)iron, pentacarbonyliron, nonacarbonyldiiron, dodecacarbonyltriiron, and disodium tetracarbonylferrate.

The palladium catalyst, cobalt catalyst and/or iron catalyst is/are used in an amount of 0.0001 to 0.5 mol, preferably 0.0005 to 0.1 mol, per mole of the reaction substrate for obtaining the objective product in good yield.

The ligands, such as phosphine, may previously be coordinated or oxidatively added to the center metal, or the catalyst may be produced by adding a requisite amount of the ligand(s) to, for example, a metal chloride. A combination of a ligand-containing metal complex and an additional ligand can also be used as a catalyst.

The ligand includes phosphine ligands, such as triphenylphosphine, trimethylphosphine, triethylphosphine, triethylphosphine, tripropylphosphine, triisopropylphosphine, tributylphosphine, dimethylphenylphosphine, diethylphenylphosphine, dibutylphenylphosphine, tri-o-tolylphosphine, tri-o-methoxyphenylphosphine, tricyclohexylphosphine, 1,2-bis (diphenylphosphino)ethane, 1,3-bis(diphenylphosphino) propane, 1,4-bis(diphenylphosphino)butane, and tris (dimethylamino) phosphine; phosphite ligands, such as trimethyl phosphite, triphenyl phosphite, and triethyl phosphite; olefins, such as cycloocta-1,5-diene, norbornadiene, norbornene, ethylene, dibenzylideneacetone, and maleic anhydride; acetato, trifluoroacetato, acetylacetonato; isocyanide ligands, such as t-butylisocyanide, cyclohexylisocyanide, and methylisocyanide; a chlorine atom, a bromine atom, an iodine atom, and a cyano group. For obtaining the objective compound in good yield, the ligand is used in an amount of not more than 10 equivalents, preferably 0.5 to 5 equivalents, to the metal serving as a catalyst.

The reaction for producing the 3-isochromanones is carried out in the presence of a hydrogen halide capturing agent. Any basic substance functioning as a hydrogen halide capturing agent can be used. Examples include alkali metal inorganic bases, alkaline earth metal inorganic bases, and tertiary amines. The alkali metal inorganic bases include sodium hydroxide, potassium hydroxide, lithium hydroxide, sodium carbonate, potassium carbonate, sodium hydrogencarbonate, potassium hydrogencarbonate, and sodium acetate. The alkaline earth metal inorganic bases include calcium hydroxide, calcium oxide, magnesium hydroxide, barium hydroxide, strontium hydroxide, and magnesium carbonate. The tertiary amines include pyridine, triethylamine, trimethylamine, and tri-n-butylamine. Of these bases, inorganic bases, such as alkali metal inorganic bases and alkaline earth metal inorganic bases, are preferred. In particular, alkaline earth metal inorganic bases, such as calcium hydroxide, are still preferred for better yield. The amount of the base to be used for obtaining the objective compound in good yield is 1 to 10 molar equivalents to the reaction substrate.

Carbon monoxide, a reaction reagent in the production of the 3-isochromanones, is used in an amount necessary for performing the reaction with no limitation on its pressure. It is preferable for producing 3-isochromanoes in a short time with good yield and selectivity that the reaction be conducted under a reaction pressure (inclusive of the carbon monoxide partial pressure) not lower than atmospheric pressure. Carbon monoxide can be used in combination with an inert gas causing no harm to the reaction, such as nitrogen gas.

Water, which is another reaction reagent for the production of the 3-isochromanones, may be present in the reaction system from the start of the reaction, but it is more effective from the viewpoint of reaction yield that the reaction be performed while gradually adding water to the reaction system. The manner of slow addition of water is not particularly restricted. A requisite amount of water can be added dropwise continuously, or a requisite amount of water can be added in several appropriately divided portions at time intervals. The rate of adding water, while dependent on the reaction conditions, is selected from the range of from 1 to 100 g/hr-mol for obtaining the objective compound in good yield. In portionwise addition, the requisite amount of water is divided in several portions corresponding to this feed rate.

Water is preferably used in an amount of not less than 3.0 molar equivalents to the reaction substrate. If the amount of water is too small, the reaction does not complete.

The reaction is carried out in an organic solvent. An alcohol having 3 to 10 carbon atoms is a preferred solvent from the standpoint of reaction efficiency. A mixed solvent of the alcohol and an ether solvent, such as tetrahydrofuran, 1,4-dioxane or diethyl ether, can also be used. Examples of the alcohol solvents having 3 to 10 carbon atoms are propyl alcohol, isopropyl alcohol, butyl alcohol, sec-butyl alcohol, isobutyl alcohol, t-butyl alcohol, pentyl alcohol, 2-pentyl alcohol, 3-pentyl alcohol, 2-methyl-2-butyl alcohol, 3-methyl-2-butyl alcohol, hexyl alcohol, 2-hexyl alcohol, 3-hexyl alcohol, 2,3-dimethyl-2-butyl alcohol, 2-methyl-2-pentyl alcohol, 4-methyl-2-pentyl alcohol, heptyl alcohol, 3-heptyl alcohol, 2-methyl-2-hexyl alcohol, 3-methyl-3-hexyl alcohol, octyl alcohol, 2-octyl alcohol, 3-octyl alcohol, 4-octyl alcohol, nonyl alcohol, 1-methyl-1-octyl alcohol, decyl alcohol, 2-decyl alcohol, cyclopentyl alcohol, cyclohexyl alcohol, 1-methyl-1-cyclohexyl alcohol, 1-ethyl-1-cyclohexyl alcohol, menthol, and borneol. Isopropyl alcohol, butyl alcohol, sec-butyl alcohol, t-butyl alcohol, and 2-methyl-2-butyl alcohol are preferred for their availability and smooth progress of the reaction.

Because of the presence of water, the reaction system is a water/organic solvent two-phase reaction system. Therefore, the reaction is conducted under vigorous stirring to attain a good yield. The term "vigorous stirring" as used herein means such agitation as achieved by rotating stirring wings at a speed of 500 rpm or higher in a cylindrical reaction vessel with no baffle plate, the wings having a diameter of about ⅓ to ⅗ of the diameter of the reaction vessel.

If desired, the reaction progress can be improved by using a phase transfer catalyst. The phase transfer catalysts include anionic surface active agents, such as alkylsufonates, alkylbenzenesulfonates, alkylnaphthalenesulfonates, alkylsulfates, alkylphosphates, and alkyl ether phosphates; cationic surface active agents, such as aliphatic quaternary ammonium salts, aromatic quaternary ammonium salts, and heterocyclic quaternary ammonium salts; amphoteric surface active agents; and nonionic surface active agents. Among these, preferred are generally employed alkylsulfonates, alkylbenzenesulfonates, alkylsulfates, and quaternary ammonium salts for their availability.

Examples of the sulfonates and sulfates are sodium 1-butanesulfonate, sodium 1-pentanesulfonate, sodium 1-hexanesulfonate, sodium 1-heptanesulfonate, sodium 1-octanesulfonate, sodium 1-nonanesulfonate, sodium 1-decanesulfonate, sodium 1-undecanesulfonate, sodium 1-dodecanesulfonate, sodium 1-tridecanesulfonate, sodium 4-octylbenzenesulfonate, sodium dodecylbenzenesulfonate, sodium 1-naphthalenesulfonate, sodium 2-naphthalenesulfonate, sodium 1,5-diisopropylnaphthalenesulfonate, sodium 1,5-di(sec-butyl)- naphthalenesulfonate, sodium dodecylsulfate, sodium tridecylsulfate, sodium 7-ethyl-2-methylundecylsulfate, and sodium polyoxyethylene(nonylphenyl)ether sulfate, and potassium salts corresponding to these sodium salts.

Examples of the quaternary ammonium salts are tetramethylammonium chloride, tetramethylammonium bromide, tetramethylammonium iodide, tetramethylammonium borofluoride, tetramethylammonium perchlorate, tetramethylammonium borofluoride, tetramethylammonium p-toluenesulfonate, tetraethylammonium chloride, tetraethylammonium bromide, tetraethylammonium iodide, tetraethylammonium borofluoride, tetraethylammonium perchlorate, tetraethylammonium borofluoride, tetraethylammonium p-toluenesulfonate, tetraethylammonium trifluoromethanesulfonate, tetrapropylammonium chloride, tetrapropylammonium bromide, tetrapropylammonium iodide, tetrabutylammonium chloride, tetrabutylammonium bromide, tetrabutylammonium iodide, tetrabutylammonium fluoride, tetrabutylammonium borofluoride, tetrabutylammonium perchlorate, tetrabutylammonium sulfate, tetrabutylammonium p-toluenesulfonate, tetrapentylammonium chloride, tetrapentylammonium bromide, tetrapentylammonium iodide, tetrahexylammonium chloride, tetrahexylammonium bromide, tetrahexylammonium iodide, tetraheptylammonium chloride, tetraheptylammonium bromide, tetraheptylammonium iodide, tetraoctylammonium bromide, tetraoctylammonium iodide, tetraphenylammonium chloride, tetraphenylammonium bromide, tetraphenylammonium iodide, methyltrioctylammonium chloride, dodecyltrimethylammonium chloride, benzyltributylammonium chloride, benzyltriethylammonium chloride, benzyltriethylammonium bromide, ethyltripropylammonium iodide, phenyltrimethylammonium chloride, phenyltrimethylammonium bromide, phenyltriethylammonium chloride, dodecylbenzyldimethylammonium bromide, cetyltriethylammonium bromide, hexadecapyridinium bromide, tetrabutylammonium hydroxide, and benzyltrimethylammonium hydroxide.

While not particularly limiting, the phase transfer catalyst is used in an amount of 0.001 to 0.03 mol per mole of the starting material for obtaining 3-isochromanones (1) in good yield.

The reaction temperature usually ranges from 0° to 120° C. while varying depending on the catalyst, base, solvent, etc. used in the reaction. For smooth progress of the reaction, the temperature is preferably selected from room temperature to 100° C.

After completion of the carbonylation reaction, the produced o-hydroxymethylphenylacetic acid salt is collected by filtration, to which an acid, such as hydrochloric acid, is added to cause esterification within the molecule. The 3-isochromanones produced are isolated through ordinary operations, such as extraction, concentration, column purification, and the like. Alternatively, an acid, e.g., hydrochloric acid, can be added directly to the reaction mixture, and the insoluble matter is separated by filtration, and the 3-isochromanones are isolated through ordinary operations, such as extraction, concentration, and column purification.

The catalyst used in the above reaction can be separated as follows. The carbonylation reaction mixture is filtered to separate a solid mixture of the catalyst and the o-hydroxymethylphenylacetic acid salt, and an acid, e.g., hydrochloric acid, is added to the mixture, followed by filtration to separate the spent catalyst as an insoluble matter. The collected catalyst is suspended in hydrochloric acid, and chlorine gas is introduced to oxidize the catalyst to recover as a hydrochloride of a metal chloride. Alternatively, an acid, e.g., hydrochloric acid, is added directly to the reaction mixture, and chlorine gas is introduced therein to oxidize the catalyst. After an organic matter containing the produced 3-isochromanones is isolated by extraction, the aqueous solution of a hydrochloride of a metal chloride is concentrated, and an appropriate amount of an alcohol solvent, e.g., ethanol, and of a ligand, e.g., triphenylphosphine, are added thereto. The precipitated complex is collected by filtration.

The 3-isochromanone derivative (1) obtained by the process of the present invention is allowed to react with, for example, trimethyl orthoformate and a boron trifluoride diethyl ether complex, and the product is allowed to react with hydrochloric acid to provide 4-(α-methoxy)methylene-3-isochromanone or 4-(α-hydroxy)-methylene-3-isochromanone in good yield (see Reference Examples 1 and 2), which can be an intermediate for the production of fungicides for agricultural use (see, e.g., WO 95/25729-A).

BEST MODE FOR CARRYING OUT THE INVENTION

The present invention will now be illustrated in greater detail by way of Reference Examples and Examples, but it should be understood that the present invention is not limited thereto.

EXAMPLE 1

In a 200 cc flask equipped with a stirrer, a thermometer, a tube for introducing hydrogen chloride, and an exhaust gas trap were charged 71.2 g (2.22 mol) of methyl alcohol and 17.8 g (0.116 mol) of 3-isochromanone (purity: 96.9%). Into the mixture was introduced 65.6 g (1.80 mol) of hydrogen chloride over a 6-hour period while vigorously stirring the mixture at a temperature of 10° to 20° C. Methyl alcohol was removed by evaporation under reduced pressure, and 100 ml of ethyl ether and 50 ml of water were added thereto to separate into an organic layer and an aqueous layer. Ethyl ether was evaporated from the organic layer, and the oily residue was distilled under reduced pressure to collect the fraction having a boiling point of 115° C. (3 mmHg) (22.5 g). As a result of analyses with a gas chromatograph and a mass spectrometer, the product was confirmed to be methyl 2-(chloromethyl)phenylacetate. The purity of the product was found to be 96.4% (yield: 93.8%).

EXAMPLE 2

To a solution of 1.0 g (6.75 mmol) of 3-isochromanone in 10 ml of toluene was added 2.68 ml (29.7 mmol) of dichloromethyl methyl ether, followed by stirring at room temperature for 24 hours. A mixed solution of 3 ml of methyl alcohol and 1.1 ml of pyridine was added thereto at room temperature. After stirring for an additional 2 hour period, 20 ml of 1N hydrochloric acid was added thereto, and the reaction mixture was extracted with three 20 ml portions of ethyl ether. The ether extracts were combined and washed with two 20 ml portions of 1N hydrochloric acid. Ethyl ether was removed by evaporation, and the residue was purified with silica gel column chromatography (ethyl acetate:hexane=1:4) to obtain 0.912 g (yield: 68.0%) of pure methyl 2-(chloromethyl)phenylacetate.

EXAMPLE 3

To a solution of 1.0 g (6.75 mmol) of 3-isochromanone in 10 ml of toluene was added 2.68 ml (29.7 mmol) of dichloromethyl methyl ether, and the mixture was stirred at 60° C. for 24 hours. After cooling to room temperature, a mixed solution of 3 ml of methyl alcohol and 1.1 ml of pyridine was added thereto, followed by further stirring at room temperature for 24 hours. To the reaction mixture was added 20 ml of 1N hydrochloric acid, followed by extraction with 20 ml of ethyl ether. The combined ether extract was washed with two 20 ml portions of 1N hydrochloric acid. Ethyl ether was evaporated, and the residue was purified with silica gel column chromatography (ethyl acetate:hexane=1:4) to obtain 1.034 g (yield: 77.1%) of pure methyl 2-(chloromethyl)phenylacetate.

EXAMPLE 4

In a 300 cc stainless steel-made autoclave were charged 175 mg (0.250 mmol) of dichlorobis(triphenylphosphine) palladium, 145 mg (0.555 mmol) of triphenylphosphine, 8.75 g (50.0 mmol) of α,α'-o-xylene dichloride, 7.80 g (105 mmol) of calcium hydroxide, 8.0 ml of water, and 100 g of t-butyl alcohol. The atmosphere inside the autoclave was displaced with carbon monoxide three times. The reaction mixture was stirred at 70° C. for 1 hour in a carbon monoxide atmosphere at 2 atm (gauge pressure: 1 kg/cm$^2$). After the reaction, the mixture was cooled to room temperature, and 100 ml of water was added thereto, followed by filtration to separate into an insoluble solid and an alkaline filtrate. The alkaline filtrate was washed with two 25 ml portions of ethyl ether, and the aqueous layer was made acidic by addition of 30 ml of concentrated hydrochloric acid and extracted with two 100 ml portions of ethyl ether. A 3N-hydrochloric acid was also added to the separated insoluble solid, the insoluble palladium catalyst was removed by filtration, and the filtrate was extracted with two 50 ml portions of ethyl ether. All the ethyl ether extracts were combined and concentrated under reduced pressure to obtain 5.65 g (yield: 76.7%) of 3-isochromanone.

The ether washing of the alkaline filtrate was evaporated under reduced pressure to remove the solvent and the like to recover 0.273 g of o-xylene dichloride.

Melting point: 76°–77° C.; $^1$H-NMR (CDCl$_3$, TMS, ppm): δ 3.70 (2H, s), 5.33 (2H, s), 7.33 (4H, s)

EXAMPLE 5

In a 300 cc round flask were put 350 mg (0.500 mmol) of dichlorobis(triphenylphosphine)palladium, 290 mg (1.11 mmol) of triphenylphosphine, 7.80 g (105 mmol) of calcium hydroxide, and 100 g of t-butyl alcohol. After displacing the atmosphere with carbon monoxide three times, the mixture was stirred at 70° C. for 1 hour in a carbon monoxide atmosphere under atmospheric pressure. Then 8.75 g (50.0 mmol) of α,α'-o-xylene dichloride was added, and the stirring was continued for an additional 3 hour period at the same temperature under atmospheric pressure of carbon monoxide. To the mixture were added one 1.0 ml portion and four 2.0 ml portions of water in this order at intervals of 3, 2, 2, and 2 hours, and the stirring was continued. The total amount of water added was 9.0 ml. After completion of the reaction (21 hours' reacting), it was confirmed with gas chromatography that the starting material had completely disappeared. The reaction mixture was cooled to room temperature, and 100 ml of water was added, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the separated insoluble solid, and the insoluble palladium catalyst was separated by filtration. The filtrate was extracted with two 50 ml portions of ethyl ether. All the ethyl ether extracts were combined and concentrated under reduced pressure to obtain 6.43 g (yield: 87.4%) of 3-isochromanone.

EXAMPLE 6

In a 100 ml flask equipped with a stirrer, a thermometer, and a tube for introducing carbon monoxide were charged 8.75 g (0.05 mol) of α,α'-o-xylene dichloride, 20 g of butyl alcohol as a solvent, 6.3 g (0.16 mol) of sodium hydroxide, 25.2 g of water, 0.58 g of tetrakis(triphenylphosphine) palladium, and 0.04 g of sodium 1-heptanesulfonate as a phase transfer catalyst. The mixture was vigorously stirred while maintaining the inner temperature at 70° C. in a carbon monoxide atmosphere. After 3 hours, the reaction mixture in the flask was separated into an organic layer and an aqueous layer. The aqueous layer was rendered acidic with hydrochloric acid and extracted with ethyl ether. The carbon monoxide absorption during the 3 hours' reacting was about 700 ml. The resulting ether extract was evaporated under reduced pressure to remove ethyl ether to afford crystals weighing 4.1 g (yield: about 55%). Gas chromatographic analysis on the crystals showed that the product was 3-isochromanone. The structure was confirmed through NMR and IR analyses. The purity was found to be 96.2%.

EXAMPLE 7

In a flask were charged 8.75 g (0.05 mol) of α,α'-o-xylene dichloride, 100 g of t-butyl alcohol as a solvent, 12.1 g of calcium hydroxide, 2.8 g of water, 0.35 g of bis (triphenylphosphine)palladium (II) chloride, 0.29 g of triphenylphosphine, and 0.13 g of benzyltriethylammonium chloride as a phase transfer catalyst. After displacing the inside of the flask with carbon monoxide, the mixture was vigorously stirred at 70° C. in a carbon monoxide atmosphere. After 17 hours' reacting, the insoluble calcium hydroxide was separated by filtration, and the filtrate was treated in the same manner as in Example 6 to obtain 4.7 g (yield: 63.5%) of 3-isochromanone. The purity was 99.0% as analyzed with gas chromatography. To the insoluble matter separated by filtration was added diluted hydrochloric acid, followed by extraction with ethyl ether. The ethyl ether extract was concentrated under reduced pressure to obtain 0.8 g of 3-isochromanone (purity: 97%). So, the total yield was 74.3%.

EXAMPLE 8

The procedure of Example 6 was repeated, except for replacing α,α'-o-xylene dichloride with 13.2 g (0.05 mol) of α,α'-o-xylene dibromide and replacing butyl alcohol with 20 g of t-butyl alcohol. As a result, 2.9 g (yield: 39.2%) of 3-isochromanone was obtained. The purity of the product was 95.1% as measured by gas chromatographic analysis.

EXAMPLE 9

The procedure of Example 6 was repeated, except for replacing butyl alcohol with 20 g of t-butyl alcohol to obtain 3.0 g (yield: 40.2%) of 3-isochromanone.

EXAMPLE 10

The procedure of Example 6 was repeated, except for replacing tetrakis(triphenylphosphine)palladium with pentacarbonylbis(triphenylphosphine)cobalt and replacing sodium 1-heptanesulfonate with benzyltrimethylammonium chloride, to obtain 0.5 g (yield: 6.7%) of 3-isochromanone.

EXAMPLE 11

In a 300 cc round flask were put 350 mg (0.500 mmol) of dichlorobis(triphenylphosphine)palladium, 290 mg (1.11 muol) of triphenylphosphine, 7.80 g (105 mmol) of calcium hydroxide, and 100 g of t-butyl alcohol. After displacing the atmosphere with carbon monoxide three times, the mixture was stirred at 70° C. for 1 hour in a carbon monoxide atmosphere under atmospheric pressure. Then 8.75 g (50.0 mmol) of α,α'-o-xylene dichloride and 3.0 ml of water were added, and the mixture was vigorously stirred for 21 hours at 70° C. in a carbon monoxide atmosphere under atmospheric pressure. The reaction mixture was cooled to room temperature, and 100 ml of water was added, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the insoluble solid separated by filtration, and the insoluble palladium catalyst was separated by filtration. The filtrate was extracted with two 50 ml portions of ethyl ether. All the ethyl ether extracts were combined and concentrated under reduced pressure to obtain 4.02 g (yield: 54.6%) of 3-isochromanone. The ether washing of the alkaline filtrate was evaporated under reduced pressure to remove the solvent and the like to recover 2.11 g of α,α'-o-xylene dichloride.

EXAMPLE 12

In a 300 cc round flask were put 350 mg (0.500 mmol) of dichlorobis(triphenylphosphine)palladium, 290 mg (1.11 mmol) of triphenylphosphine, 7.80 g (105 mmol) of calcium hydroxide, and 100 g of 2-methyl-2-propanol. After displacing the atmosphere with carbon monoxide three times, the mixture was stirred at 70° C. for 1 hour in a carbon monoxide atmosphere under atmospheric pressure. Then 8.75 g (50.0 mmol) of α,α'-o-xylene dichloride and 8.0 ml of water were added, and the mixture was vigorously stirred for 11 hours at 70° C. in a carbon monoxide atmosphere under atmospheric pressure. The reaction mixture was cooled to room temperature, and 100 ml of water was added, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the insoluble solid separated by filtration, and the insoluble palladium catalyst was separated by filtration. The filtrate was extracted with two 50 ml portions of ethyl ether. All the ethyl ether extracts were combined and concentrated under reduced pressure to afford 3.80 g (yield: 51.3%) of 3-isochromanone. The ether washing of the alkaline filtrate was evaporated under reduced pressure to remove the solvent and the like to recover 2.53 g of α,α'-o-xylene dichloride.

EXAMPLE 13

In a 300 cc round flask were put 350 mg (0.500 mmol) of dichlorobis(triphenylphosphine)palladium, 290 mg (1.11 mmol) of triphenylphosphine, 7.80 g (105 mmol) of calcium hydroxide, and 100 g of t-butyl alcohol. After displacing the atmosphere with carbon monoxide three times, the mixture was stirred at 70° C. for 1 hour in a carbon monoxide atmosphere under atmospheric pressure. Then 8.75 g (50.0 mmol) of α,α'-o-xylene dichloride and 3.0 ml of water were added. A 2.0 ml portion of water was further added thereto 5 times for every 2 hours. Meanwhile the reaction mixture was kept stirred vigorously at 70° C. under atmospheric pressure of carbon monoxide for a total period of 11 hours. The total amount of water added was 13.0 ml. After confirming complete disappearance of the starting material by gas chromatography, the reaction mixture was cooled to room temperature, and 100 ml of water was added, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the insoluble solid separated by filtration, and the insoluble palladium catalyst was separated by filtration. The filtrate was extracted with two 50 ml portions of ethyl ether. All the ethyl ether extracts were combined and concentrated under reduced pressure to furnish 5.98 g (yield: 81.2%) of 3-isochromanone.

EXAMPLE 14

In a 300 cc round flask were charged 350 mg (0.500 mmol) of dichlorobis(triphenylphosphine)palladium, 290 mg (1.11 mmol) of triphenylphosphine, 7.80 g (105 mmol) of calcium hydroxide, and 100 g of 2-methyl-2-propanol. After displacing the atmosphere with carbon monoxide three times, the mixture was stirred at 70° C. for 1 hour in a carbon monoxide atmosphere under atmospheric pressure. Then 8.75 g (50.0 mmol) of α,α'-o-xylene dichloride and 20 ml of water were added, and the mixture was vigorously stirred for 11 hours period at 70° C. in a carbon monoxide atmosphere under atmospheric pressure. The reaction mixture was cooled to room temperature, and 100 ml of water was added, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the insoluble solid separated by filtration, and the insoluble palladium catalyst was separated by filtration. The filtrate was extracted with two 50 ml portions of ethyl ether. All the ethyl ether extracts were combined and concentrated under reduced pressure to obtain 4.26 g (yield: 57.6%) of 3-isochromanone. The ether washing of the alkaline filtrate was evaporated under reduced pressure to remove the solvent and the like to recover 2.94 g of α,α'-o-xylene dichloride.

EXAMPLE 15

In a 300 cc round flask were put 350 mg (0.500 mmol) of dichlorobis(triphenylphosphine)palladium, 290 mg (1.11 mmol) of triphenylphosphine, 7.80 g (105 mmol) of calcium hydroxide, and 50 g of t-butyl alcohol. After displacing the atmosphere with carbon monoxide three times, the mixture was stirred at 70° C. for 1 hour in a carbon monoxide atmosphere under atmospheric pressure. Then 8.75 g (50.0 mmol) of α,α'-o-xylene dichloride and 3.0 ml of water were added. A 2.0 ml portion of water was further added thereto 5 times for every 2 hours. Meanwhile the reaction mixture was kept stirred vigorously at 70° C. for 11 hours under atmospheric pressure of carbon monoxide. The total amount of water added was 13.0 ml. After confirming complete disappearance of the starting material by gas chromatography, the reaction mixture was cooled to room temperature, and 100 ml of water was added, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the insoluble solid separated by filtration, and the insoluble palladium catalyst was separated by filtration. The filtrate was extracted with two 50 ml portions of ethyl ether. All the ethyl ether extracts were combined and concentrated under reduced pressure to furnish 6.01 g (yield: 81.6%) of 3-isochromanone.

EXAMPLE 16

In a 300 cc round flask were put 350 mg (0.500 mmol) of dichlorobis(triphenylphosphine)palladium, 290 mg (1.11 mmol) of triphenylphosphine, 7.80 g (105 mmol) of calcium hydroxide, and 100 g of t-butyl alcohol. After displacing the atmosphere with carbon monoxide three times, the mixture was stirred at 70° C. for 1 hour in a carbon monoxide atmosphere under atmospheric pressure. Then 8.75 g (50.0 mmol) of $\alpha,\alpha'$-o-xylene dichloride and 2.0 ml of water were added. The reaction mixture was kept stirred vigorously at 70° C. for 12 hours under atmospheric pressure of carbon monoxide while dropwise adding water at a rate of 16 ml/12 hours. After confirming complete disappearance of the starting material by gas chromatography, the reaction mixture was cooled to room temperature, 50 ml of water, 100 ml of monochlorobenzene, and 30 ml of concentrated hydrochloric acid were added thereto, and chlorine gas was introduced for 5 minutes. The reaction mixture was separated into an acidic aqueous layer and an organic layer. The organic layer was concentrated under reduced pressure, and the residue was recrystallized from toluene/hexane (2.5/1) to obtain 6.11 g (yield: 82.5%) of 3-isochromanone. On the other hand, the acidic aqueous layer was concentrated under reduced pressure, and the residue was suspended in 50 ml of ethanol. To the suspension was added 600 mg of triphenylphosphine, followed by stirring for 2 hours. The precipitated solid was isolated by filtration and washed successively with 50 ml of water and 50 ml of ethyl ether to afford 341 mg of dichlorobis(triphenylphosphine)palladium.

EXAMPLE 17

Into a 2000 cc round flask were put 2.00 g (2.85 mmol) of dichlorobis(triphenylphosphine)palladium, 1.66 g (6.33 mmol) of triphenylphosphine, 89.1 g (1.20 mol) of calcium hydroxide, and 860 g of t-butyl alcohol. After displacing the atmosphere with carbon monoxide three times, the mixture was stirred at 70° C. for 1 hour in a carbon monoxide atmosphere at 2 atm (gauge pressure: 1 kg/cm$^2$). Then 100 g (571 mmol) of $\alpha,\alpha'$-o-xylene dichloride and 22.5 ml of water were added. A 10 ml portion of water was further added thereto 13 times for every 30 minutes. Meanwhile the reaction mixture was kept stirred vigorously for 7 hours at 70° C. in a carbon monoxide atmosphere under 2 atmospheres (gauge pressure: 1 kg/cm$^2$). After confirming complete disappearance of the starting material by gas chromatography, the reaction mixture was cooled to room temperature, and 500 ml of water, 300 ml of toluene, and 200 ml of concentrated hydrochloric acid were added thereto. The insoluble solid was separated by filtration, and the filtrate was separated into an acidic aqueous layer and an organic layer. The organic layer was extracted with 400 ml of a 15% sodium hydroxide aqueous solution. To the resulting alkaline aqueous layer was added 200 ml of concentrated hydrochloric acid, and the mixture was again extracted with three 150 ml portions of toluene. The toluene extracts were combined and concentrated under reduced pressure to furnish 71.7 g (yield: 84.7%) of 3-isochromanone.

EXAMPLE 18

In a 5000 cc round flask were put 6.00 g (8.55 mmol) of dichlorobis(triphenylphosphine)palladium, 4.97 g (19.0 mmol) of triphenylphosphine, 287 g (3.60 mol) of calcium hydroxide, 300 g (1.71 mol) of $\alpha,\alpha'$-o-xylene dichloride, and 2.58 kg of t-butyl alcohol. After displacing the atmosphere with carbon monoxide three times, the mixture was heated to 70° C., and 70 ml of water was added thereto in a carbon monoxide atmosphere at 1.5 atm (gauge pressure: 0.5 kg/cm$^2$). Eighteen 30 ml portions of water were further added thereto for every 30 minutes. Meanwhile the reaction system was vigorously stirred for a total period of 9.5 hours. After confirming complete disappearance of the starting material by gas chromatography, the reaction mixture was cooled to room temperature, and 800 ml of water was added thereto, followed by filtration to separate the insoluble solid. The resulting alkaline filtrate was washed with two 600 ml portions of toluene. The aqueous layer was rendered acidic by addition of 400 ml of concentrated hydrochloric acid and extracted with three 800 ml portions of toluene. The toluene extract was concentrated under reduced pressure to afford 210.2 g (yield: 83.0%) of 3-isochromanone.

EXAMPLE 19

Into a 300 cc round flask were put 350 mg (0.500 mmol) of dichlorobis(triphenylphosphine)palladium, 290 mg (1.11 mmol) of triphenylphosphine, 7.80 g (105 mmol) of calcium hydroxide, and 100 g of t-butyl alcohol. After displacing the atmosphere with carbon monoxide three times, the mixture was stirred at 70° C. for 1 hour in a carbon monoxide atmosphere under atmospheric pressure. Then 8.75 g (50.0 mmol) of $\alpha,\alpha'$-o-xylene dichloride and 3.0 ml of water were added, and reaction mixture was vigorously stirred at 70° C. for 21 hours under atmospheric pressure of carbon monoxide. The reaction mixture was cooled to room temperature, and 100 ml of water was added thereto, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the separated insoluble solid, and the insoluble palladium catalyst was separated by filtration. The filtrate was extracted with two 50 ml portions of ethyl ether. All the ethyl ether extracts were combined and concentrated under reduced pressure to obtain 4.02 g (yield: 54.6%) of 3-isochromanone. The ether washing of the alkaline filtrate was evaporated under reduced pressure to remove the solvent and the like to recover 2.11 g of the o-xylene dichloride.

EXAMPLE 20

In a 300 cc round flask were put 350 mg (0.500 mmol) of dichlorobis(triphenylphosphine)palladium, 290 mg (1.11 mmol) of triphenylphosphine, 7.80 g (105 mmol) of calcium hydroxide, and 100 g of t-butyl alcohol. After displacing the atmosphere with carbon monoxide three times, the mixture was stirred at 70° C. for 1 hour in a carbon monoxide atmosphere under atmospheric pressure. Then 8.75 g (50.0 mmol) of $\alpha,\alpha'$-o-xylene dichloride and 8.0 ml of water were added, and reaction mixture was vigorously stirred at 70° C. for 11 hours under atmospheric pressure of carbon monoxide. After the reaction, the reaction mixture was cooled to room temperature, and 100 ml of water was added thereto, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the separated insoluble solid, and the insoluble palladium catalyst was separated by filtration. The filtrate was extracted with two 50 ml portions of ethyl ether. All the ethyl ether extracts were combined and concentrated under reduced pressure to obtain 3.80 g (yield: 51.3%) of 3-isochromanone. The ether washing of the alkaline filtrate was evaporated under reduced pressure to remove the solvent and the like to recover 2.53 g of the o-xylene dichloride.

EXAMPLE 21

In a 300 cc round flask were put 350 mg (0.500 mmol) of dichlorobis(triphenylphosphine)palladium, 290 mg (1.11 mmol) of triphenylphosphine, 7.80 g (105 mmol) of calcium hydroxide, and 100 g of t-butyl alcohol. After displacing the atmosphere with carbon monoxide three times, the mixture was stirred at 70° C. for 1 hour in a carbon monoxide atmosphere under atmospheric pressure. Then 8.75 g (50.0 mmol) of α,α'-o-xylene dichloride and 20 ml of water were added, and reaction mixture was vigorously stirred at 70° C. for 11 hours under atmospheric pressure of carbon monoxide. After the reaction, the reaction mixture was cooled to room temperature, and 100 ml of water was added thereto, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the separated insoluble solid, and the insoluble palladium catalyst was separated by filtration. The filtrate was extracted with two 50 ml portions of ethyl ether. All the ethyl ether extracts were combined and concentrated under reduced pressure to obtain 4.26 g (yield: 57.6%) of 3-isochromanone. The ether washing of the alkaline filtrate was evaporated under reduced pressure to remove the solvent and the like to recover 2.94 g of the o-xylene dichloride.

EXAMPLE 22

In a 300 cc stainless steel-made autoclave were charged 350 mg (0.500 mmol) of dichlorobis(triphenylphosphine) palladium, 290 mg (1.11 mmol) of triphenylphosphine, 8.75 g (50.0 mmol) of α,α'-o-xylene dichloride, 7.80 g (105 mmol) of calcium hydroxide, 3.0 ml of water, and 100 g of t-butyl alcohol. After displacing the atmosphere with carbon monoxide three times, the mixture was stirred at 70° C. for 10 hours under 2 atm of carbon monoxide (gauge pressure: 1 kg/cm$^2$). After the reaction, the reaction mixture was cooled to room temperature, and 100 ml of water was added thereto, followed by filtration to separate into an insoluble solid and an alkaline filtrate. The alkaline filtrate was washed with two 25 ml portions of ethyl ether, made acidic by addition of 30 ml of concentrated hydrochloric acid, and extracted with two 100 ml portions of ethyl ether. On the other hand, 3N hydrochloric acid was added to the separated insoluble solid, and the insoluble palladium catalyst was separated by filtration. The filtrate was extracted with two 50 ml portions of ethyl ether. All the ethyl ether extracts were combined and concentrated under reduced pressure to obtain 4.28 g (yield: 58.1%) of 3-isochromanone. The ether washing of the alkaline filtrate was evaporated under reduced pressure to remove the solvent and the like to recover 1.67 g of the o-xylene dichloride.

EXAMPLE 23

In a 300 cc stainless steel-made autoclave were put 350 mg (0.500 mmol) of dichlorobis(triphenylphosphine) palladium, 290 mg (1.11 mmol) of triphenylphosphine, 8.75 g (50.0 mmol) of α,α'-o-xylene dichloride, 7.80 g (105 mmol) of calcium hydroxide, 15.0 ml of water, and 150 g of t-butyl alcohol. After displacing the atmosphere with carbon monoxide three times, the mixture was stirred at 70° C. for 5 hours under 2 atm of carbon monoxide (gauge pressure: 1 kg/cm$^2$). The reaction mixture was cooled to room temperature, and 100 ml of water and 30 ml of concentrated hydrochloric acid were added thereto. Analysis of the reaction mixture by gas chromatography revealed production of 3-isochromanone at a yield of 72.9%.

REFERENCE EXAMPLE 1

In a flask was put 4.37 g (41.1 mmol) of trimethyl orthoformate and cooled to −30° C. A solution of 4.62 g (32.5 mmol) of a boron trifluoride diethyl ether complex in 15 ml of methylene chloride was added thereto dropwise over a period of 5 minutes. The reaction mixture was stirred at 0° C. for 20 minutes, and 20 ml of methylene chloride and 2.00 g (13.5 mmol) of 3-isochromanone were added thereto at −70° C. Then, 5.24 g (40.5 mmol) of diisopropylethylamine was added thereto over 8 minutes, followed by stirring at that temperature for 1 hour and then at room temperature for 1 hour. To the reaction mixture was added 20 ml of concentrated hydrochloric acid, followed by stirring at room temperature for 3 hours. After completion of the reaction, the reaction mixture was extracted with three 20 ml portions of chloroform. The organic layers were combined and concentrated. The residue was purified with silica gel column chromatography (ethyl acetate:hexane=4:1) to obtain 1.12 g (yield: 47.0%) of 4-(α-methoxy)methylene-3-isochromanone.

REFERENCE EXAMPLE 2

A solution of 4.37 g (41.1 mmol) of trimethyl orthoformate in 15 ml of methylene chloride was cooled to −30° C., and 4.62 g (32.5 mmol) of a boron trifluoride diethyl ether complex was added thereto. After stirring at 0° C. for 15 minutes, 20 ml of methylene chloride and 2.00 g (13.5 mmol) of 3-isochromanone were added thereto at −70° C. Then, 5.24 g (40.5 mmol) of diisopropylethylamine was added thereto dropwise over 7 minutes, followed by stirring at that temperature for 1 hour and then at room temperature for 2.5 hours. To the reaction mixture was added 50 ml of 1N hydrochloric acid, followed by stirring at room temperature for 1 hour. After completion of the reaction, the reaction mixture was extracted with two 20 ml portions of chloroform. The organic layers were combined and concentrated. The residue was purified with silica gel column chromatography (ethyl acetate:hexane=4:1) to obtain 2.30 g (yield: 89.4%) of 4-(α-methoxy)methylene-3-isochromanone.

INDUSTRIAL APPLICABILITY

According to the process of the present invention, 3-isochromanones can be produced in good yield at high selectivity by reacting an α,α'-o-xylene dihalide derivative with carbon monoxide and water in an organic solvent in the presence of a palladium catalyst and an inorganic base.

According to the process of the present invention, 2-(halomethyl)phenylacetic acid esters can be produced in good yield and selectivity by reacting the thus obtained 3-isochromanone with a hydrogen halide and an alcohol or reacting the 3-isochromanone with a dihalomethyl alkyl ether and then reacting the product with an alcohol in the presence of a base.

Production of the objective compounds with good yield and selectivity, which is characteristic of the present invention, is of great advantage in industrialization in view of simplification of equipment, reaction efficiency, and simplification of purification process.

What is claimed is:

1. A process for producing 2-(halomethyl)phenylacetic acid esters represented by the following formula (3):

wherein $R^1$ represents a hydrogen atom, a halogen atom, an alkyl group having 1 to 6 carbon atoms, or an alkyloxy group having 1 to 6 carbon atoms; $R^2$ represents an alkyl group having 1 to 6 carbon atoms; and X represents a halogen atom, which comprises:
reacting a 3-isochromanone represented by the following formula (1):

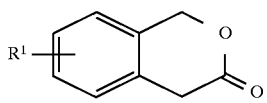

wherein $R^1$ is the same meaning as defined above,
with a dihalomethyl alkyl ether to obtain a reactant; and then
reacting the reactant with an alcohol represented by the following formula (2):

$R^2OH$   (2)

wherein $R^2$ is the same meaning as defined above, in the presence of a base.

2. The process according to claim 5, wherein said dihalomethyl alkyl ether is dichloromethyl methyl ether.

3. A process for producing 3-isochromanones represented by the following formula (1):

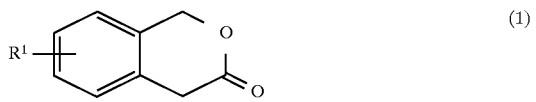

wherein $R^1$ represents a hydrogen atom, a halogen atom, an alkyl group having 1 to 6 carbon atoms, or an alkyloxy group having 1 to 6 carbon atoms, which comprises:
reacting an α,α'-o-xylene dihalide derivative represented by the following formula (4):

wherein $R^1$ is the same meaning as defined above; and X represents a halogen atom,
with carbon monoxide and water in an organic solvent in the presence of a hydrogen halide capturing agent and a catalyst to obtain a reactant; and then
treating the reactant with an acid.

4. The process according to claim 3, wherein said catalyst is selected from a palladium catalyst, a cobalt catalyst, and an iron catalyst.

5. The process according to claim 3, wherein said hydrogen halide capturing agent is an alkaline earth metal inorganic base.

6. The process according to claim 5, wherein said alkaline earth metal inorganic base is calcium hydroxide.

7. The process according to any one of claims 5 to 6, wherein said organic solvent is an alcohol having 3 to 10 carbon atoms.

8. The process according to claim 3, wherein said reacting is carried out while water is gradually added.

9. The process according to claim 4, wherein said reacting is carried out while water is gradually added.

10. The process according to claim 5, wherein said reacting is carried out while water is gradually added.

11. The process according to claim 6, wherein said reacting is carried out while water is gradually added.

12. The process according to claim 7, wherein said reacting is carried out while water is gradually added.

* * * * *